(12) United States Patent
Kasinrerk et al.

(10) Patent No.: US 8,563,330 B2
(45) Date of Patent: Oct. 22, 2013

(54) PROCESS OF SCREENING FOR ALPHA-THALASSEMIA CARRIER USING IMMUNOCHROMATOGRAPHIC STRIP TEST

(75) Inventors: Watchara Kasinrerk, Saraphee (TH); Chatchai Tayapiwatana, Bangkholeam (TH); Thanusak Tatu, Hangdong (TH); Suthat Fucharoen, Bangkoknoi (TH); Sawitree Chiampanichayakul, Sansai (TH)

(73) Assignee: National Science and Technology Development Agency, Klong Luang Pathumthani (TH)

( * ) Notice: Subject to any disclaimer, the term of this patent is extended or adjusted under 35 U.S.C. 154(b) by 853 days.

(21) Appl. No.: 12/053,449

(22) Filed: Mar. 21, 2008

(65) Prior Publication Data

US 2008/0233659 A1  Sep. 25, 2008

(30) Foreign Application Priority Data

Mar. 23, 2007  (TH) ................................ 0701001329

(51) Int. Cl.
*G01N 33/538* (2006.01)
*G01N 33/555* (2006.01)
*G01N 33/02* (2006.01)

(52) U.S. Cl.
USPC ........... 436/541; 436/514; 436/515; 436/518; 436/522; 436/523; 436/524; 436/526; 436/530; 436/538; 436/44; 436/46; 436/66; 436/164; 436/169; 435/7.1; 435/7.25; 435/69.6; 435/287.2; 435/287.7; 435/287.9; 435/288.6; 422/400; 422/408; 422/425; 422/70

(58) Field of Classification Search
USPC ............... 436/514, 518, 522, 530, 44, 46, 66, 436/164, 169, 810, 811, 515, 523, 524, 526, 436/538, 541; 435/7.1, 7.21, 7.25, 287.1, 435/287.2, 287.3, 287.7, 287.9, 288.5, 805, 435/810, 970, 7.94, 69.6, 288.6; 422/400, 422/408, 425, 62, 70
See application file for complete search history.

(56) References Cited

U.S. PATENT DOCUMENTS 6,221,678 B1 * 4/2001 Chandler ...................... 436/530

OTHER PUBLICATIONS

Kutlar et al. (Quantitation of Hb Bart's, H, Portland-I, Portland-II and constant spring by anion-exchange high-performance liquid chromatography. J. Chromatogr. 1989; 487:265-274).*
Makonkawkeyoon et al. (Production of a mouse hybridoma secreting monoclonal antibody highly specific to hemoglobin Bart's (gamma4), Lab. Hematol. 2006; 12(4): 193-200).*
Jintaridth, P et al., Chicken egg yolk antibodies specific for the gamma chain of human hemoglobin for diagnosis of thalassemia. Int. J. Hematol. Jun. 2006; 83(5): 408-14.

(Continued)

*Primary Examiner* — Gail R Gabel
(74) *Attorney, Agent, or Firm* — Dorsey & Whitney LLP

(57) ABSTRACT

The invention provides a device and method for the rapid identification of patients suspected of having thalassemia. The invention provides a test strip for the aqueous detection of thalassemia related proteins in whole blood. The test strip includes antibodies specific to the gamma 4, (γ4) protein and provides easy visual discrimination between a positive result and a negative result. The invention can be used in remote or clinical settings.

4 Claims, 4 Drawing Sheets

(56) References Cited

OTHER PUBLICATIONS

Makonkawkeyoon, L. et al. Production of a mouse hybridoma secreting monoclonal antibody highly specific to hemoglobin Bart's (gama4). Lab Hematol. 2006; 12(4): 193-200.

Abraham EC, et al. Separation of human hemoglobins by DEAE-cellulose chromatography using gycine-KCN-NaCl developers. Hemoglobin. 1976-1977; 1:27-44.

Kutlar, F. et al. Quantitation of Hb Bart's, H, Portland-I, Portland-II and constant spring by anion-exchange high-performance liquid chromatography. J. Chromatogr. 1989; 487:265-274.

* cited by examiner

PROCESS OF SCREENING FOR ALPHA-THALASSEMIA CARRIER USING IMMUNOCHROMATOGRAPHIC STRIP TEST

CROSS-REFERENCE TO RELATED APPLICATION

This application claims priority to Thai patent application number 0701001329 filed Mar. 23, 2007 which is herein incorporated in its entirety.

FIELD OF THE INVENTION

The invention provides a test strip having a primary antibody specific to alpha thalassemia and secondary antibodies that are either specific to alpha thalassemia or are specific to the monoclonal antibody. Detection is made by identification of which secondary antibody binds the primary antibody.

BACKGROUND OF THE INVENTION

Thalassemia is an autosomal recessive inherited human genetic disorder of the red blood cells (1). It reduces the amount of hemoglobin in a human body, leading to anemia (2). The alpha thalassemia results in a reduced rate of synthesis of alpha globin chain which is the main component of hemoglobin. Alpha thalassemia can be classified into four types and severity of each typed is different depending on the number of the deletion of genetic loci for alpha globin. Alpha thalassemia is commonly found in Southeast Asia, Southern China, India, the Middle East and in the Mediterranean region (3). Due to global migration patterns, there has been an increase in the incidence of thalassemia in many parts of the world (4). There are two major alpha thalassemia carriers, alpha thalassemia1 (alpha0 thalassemia) and alpha thalassemia2 (alpha+thalassemia) carriers. The two alpha globin genes on the same chromosome are deleted in alpha thalassemia1. There is only one alpha globin gene deletion in an alpha thalassemia2. Moreover, some abnormal hemoglobin such as Hb Constant Spring (Hb CS) and Hb Pakse also affect the alpha globin gene expression and behave like and alpha thalassemia2. The interaction between these abnormal genes lead to many alpha thalassemia syndromes such as homozygous alpha thalassemia, Hb H disease (alpha thalassemia1/ and alpha thalassemia2 or alpha thalassemia1/Hb CS) and Hb Bart's hydrops fetalis (homozygous alpha thalassemia1). Heterozygote screening and genetic counseling are essential for the prevention and control of severe thalassemia diseases (5).

Small amount of Hb Bart's is presented in the blood of some alpha thalassemia carriers. The immunochromatographic strip test can detect Hb Bart's in alpha thalassemia1 carrier and all other alpha thalassemia syndromes carry this abnormal gene such as Hb H disease, AE Bart's disease and Hb Bart's hydrops fetalis. The test is also positive in homozygote for alpha thalassemia2. Thus this test will help to prevent severe alpha thalassemia disorders in many populations.

The immunochromatographic strip is a qualitative, lateral flow immunoassay for the screening of various types of alpha thalassemia trait by using whole blood. As the blood test sample (hemolysate) diffuses through the absorbent test strip, the labeled antibody-colloidal gold conjugate binds to the Hb Bart's in the specimen forming an antibody-antigen complex. This complex binds to the anti Hb Bart's antibody in the test line and expresses a purple-red band. The absence of a colored band in the test region indicates a negative result. The reaction mixture continues flowing through the absorbent device past the test and control lines. Unbound conjugate binds to the reagents in the control line, producing a pink color band, demonstrating that the reagents and test strip are functioning correctly.

SUMMARY OF THE INVENTION

The immunochromatographic strip test presented in this invention is recommended for the detection of Hb Bart's protein in a human whole blood specimen. The immunochromatographic strip test shows positive reading for alpha thal 1 trait, HbH (alpha thal1/alpha thal2), HbH-CS (alpha thal1/Hb CS), AEBart's (HbH disease+HbE trait), Hb Bart's hydrops fetalis (homozygous alpha thal1) and homozygous alpha thal 2. The immunochromatographic strip test shows negative reading in the alpha thal 2 trait, beta thal trait, HbE trait and normal persons. If the test reading shows negative and clinical symptoms persist, additional follow-up testing using other laboratory methods is suggested. A negative reading at any time does not preclude the possibility of alpha thalassemia disorder. The immunochromatographic strip test has been compared with referenced method: Gap polymerase chain reaction for alpha thalassemia determination and HPLC (Variant, Bio Rad) for beta thalassemia determination. The samples included 67 cases of non-alpha thalassemia disorder and alpha thalassemia 2 trait and 41 cases of alpha thalassemia 1, homozygous alpha thalassemia2, Hb H disease and AE Bart's disease which were tested using the immunochromatographic strip test.

Therefore, in one exemplary embodiment, the invention provides a method of screening for an α-thalassemia carrier using an immunochromatographic strip comprising: (1) obtaining a blood sample from a patient suspected of carrying α-thalassemia; (2) lysing the red blood cells; (3) applying an aliquot of lysed red blood cells to an immunochromatographic strip; and (4) observing a result. Using this method, a positive result is discernable from a negative result and wherein a carrier of α-thalassemia is identified. In various exemplary embodiments according to the invention, the blood sample is mixed with a chelating agent such as but, not limited EDTA. In various exemplary embodiments, the hemolytic agent is TWEEN 20 Polysorbate 20, SDS, NP-40 nonyl phenoxypolyethoxylethanol, phenylhydrazine, TRITON X-100 octyl phenol ethoxylate, or hemolysin.

In another exemplary embodiment, the invention includes a test strip for identifying an α-thalassemia carrier comprising: a sample application pad; a conjugate releasing pad; a nitrocellulose membrane; and an absorbent pad. In this exemplary embodiment, a colloid particle conjugated antibody specific for an α thalassemia protein is applied to the conjugate releasing pad; wherein an unconjugated antibody specific for α thalassemia is applied to the nitrocellulose membrane at a capture line and an antibody specific to the α thalassemia specific antibody is applied to the nitrocellulose membrane at a control line, distal to the capture line. An α thalassemia specific protein in a sample binds to the α thalassemia specific antibody conjugated colloid particle in the conjugate pad and diffuses to the capture line and binds to the a thalassemia specific antibody. Absence of an α thalassemia specific protein in a sample diffuses the α thalassemia specific antibody conjugated colloid to the control line and binds to the antibody specific to the α thalassemia specific antibody. A positive test is identified by binding of the cc thalassemia specific antibody conjugated colloid at the capture line and a negative test is identified by binding of the α thalassemia specific antibody conjugated colloid at the control line.

In various exemplary embodiments according to the invention, the colloid particle is gold. In some embodiments, the colloid particle has a diameter of about 10-25 nm. In some embodiments, the α thalassemia specific protein is a γ4 protein. In various exemplary embodiments, a, thalassemia specific antibody is a monoclonal antibody derived from a mouse. In some exemplary embodiments, the α thalassemia specific antibody is a rabbit antibody. In still other exemplary embodiments the antibody is a polyclonal antibody.

In various other exemplary embodiments, the invention includes a kit for identifying carriers of α thalassemia. the kit including an α thalassemia test strip and instructions for use. In various exemplary embodiments, the invention further includes a lysis buffer. In still other exemplary embodiments, the kit includes a wash buffer.

In still other exemplary embodiments according to the invention, the invention includes A method of conjugating a monoclonal or a polyclonal antibody specific to for a thalassemia with a nanoparticle comprising obtaining an aqueous solution of a colloidal nanoparticle at a concentration of about $1-10 \times 10^{-3}$ M of HAuCl4, diluting the colloidal nanoparticle with water to bout 1:2 to about 1:50 to obtain a diluted solution, heating the diluted solution with stirring and adding sodium citrate to the heating solution to reduce the solution until a color change. In some exemplary embodiments, the sodium citrate has a concentration of about 0.1 to 1.0%.

In still other exemplary embodiments according to the invention, the invention includes a method of making a .alpha, thalassemia specific antibody coated colloid particle comprising, diluting a monocolonal antibody specific to .alpha-thalassemia with 1-10 mM sodium borate buffer pH 5-10 to obtain a solution, adding the solution lo 100 ml of a 0.25 mM of colloidal nanoparticle, adjusting the pH to 7.0-10.0 by the addition of 0.01 M Na2C03, stirring the mixture for 10-60 min and adding a 20% volume of 5% BSA in 5 mM NaCl, reacting approximately 5 minutes, centrifuging at 4.degree. C. for approximately 10,00 to 20,00 rpm for approximately 30, resuspending a pellet in phosphate buffer, and obtaining an antibody coated colloid particle solution.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be apparent from the description, as set forth hereinafter.

BRIEF DESCRIPTION OF THE FIGURES

Various exemplary embodiments of the compositions and methods according to the invention will be described in detail, with reference to the following figures wherein:

FIG. 2 B is a diagram showing band densities with a densitometer which illustrates the purity of lg Y heavy and light chains with molecular weights of approximately 67 kd and 28 kd.

FIG. 3A, Specificity of anti-hemoglobin (Hb) Bart's immunoglobulin Y (IgY) antibodies extracted from egg yolk. Globin chains (α, β, $^G\gamma$, and $^A\gamma$), intact Hbs (Hb A, Hb A$_2$, Hb F, and Hb Bart's), and hemolysates (normal cord, healthy adult, and Hb Bart's hydrops fetalis) were coated onto an enzyme-linked immunosorbent assay plate. Reactions were performed with the various tested antibodies. Open bars, preimmune IgY extract at 1:1000 dilution; closed bars, 1:1000 dilution of IgY extracted at the time of maximum antibody response. B, Sodium dodecyl sulfate-polyacrylamide gel electrophoresis (SDS-PAGE) analysis of IgY extracted from egg yolk. The IgY extracts from 3 egg yolks were analyzed by using 12.5% SDS-PAGE gels under reducing (lanes 2-4) and nonreducing (lanes 5-7) conditions. Markers of molecular weight (in kilodaltons) are shown in lane 1.

DETAILED DESCRIPTION OF THE EXEMPLARY EMBODIMENTS

I. In General

Figure 1:
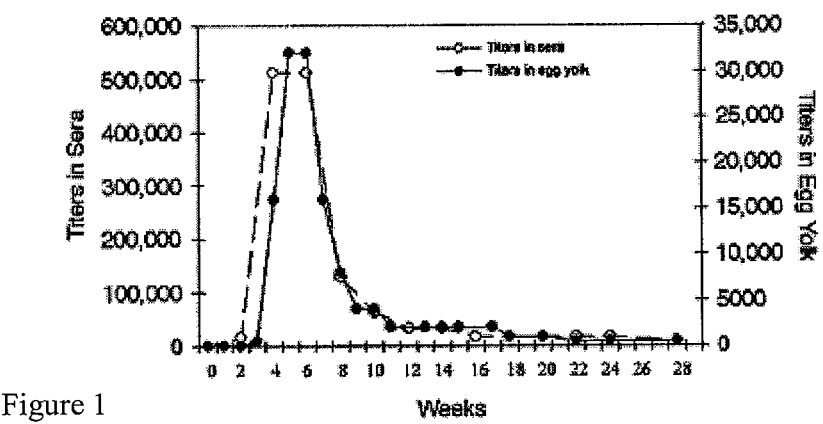
FIG. 1 Anti-hemoglobin Bart's antibody responses in chicken sera and egg yolk. Hb Bart's was inoculated at weeks 0, 2, and 4. Various dilutions of sera and immunoglobulin Y extracts (1 mg/mL) collected at various time points were measured by indirect enzyme-linked immunosorbent assay. The antibody titer was calculated as the reciprocal of the highest dilution giving positive reactivity.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The invention and the various features and advantageous details thereof are explained more fully with reference to the non-limiting embodiments that are illustrated in the accompanying drawings and detailed in the following description. Descriptions of well known components and processing techniques are omitted so as not to unnecessarily obscure the invention in detail but such descriptions are, nonetheless, included in disclosure by incorporation by reference of the citations following the Examples section. It should be understood, however, that the detailed description and the specific examples, while indicating preferred embodiments of the invention, are given by way of illustration only and not by way of limitation. Various substitutions, modifications, additions and/or rearrangements within the spirit and/or scope of the underlying inventive concept will become apparent to those skilled in the art from this detailed description.

II. The Invention

The invention thus disclosed herein, provides a device and method for the rapid identification of patients suspected of having thalassemia. The invention provides a test strip for the aqueous detection of thalassemia related proteins in whole blood. The test strip includes antibodies specific to the gamma 4, (γ4) protein and provides discrimination between a positive result and a negative result. The invention can be used in remote or clinical settings.

Therefore, in one exemplary embodiment, the invention provides a method of screening for an α-thalassemia carrier using an immunochromatographic strip comprising: (1) obtaining a blood sample from a patient suspected of carrying α-thalassemia; (2) lysing the red blood cells; (3) applying an aliquot of lysed red blood cells to an immunochromatographic strip; and (4) observing a result. Using this method, a positive result is discernable from a negative result and wherein a carrier of α-thalassemia is identified. In various exemplary embodiments according to the invention, the blood sample is mixed with a chelating agent such as but, not limited EDTA. In various exemplary embodiments, the hemolytic agent is TWEEN 20 Polysorbate 20, SDS, NP-40 nonyl phenoxypolyethoxylethanol, phenylhydrazine, TRITON X-100 octyl phenol ethoxylate, or hemolysin.

In another exemplary embodiment, the invention includes a test strip for identifying an α-thalassemia carrier comprising: a sample application pad; a conjugate releasing pad; a nitrocellulose membrane; and an absorbent pad. In this exemplary embodiment, a colloid particle conjugated antibody specific for an α thalassemia protein is applied to the conjugate releasing pad; wherein an unconjugated antibody specific for α thalassemia is applied to the nitrocellulose membrane at a capture line and an antibody specific to the α thalassemia specific antibody is applied to the nitrocellulose membrane at a control line, distal to the capture line. An α thalassemia specific protein in a sample binds to the α thalassemia specific antibody conjugated colloid particle in the conjugate pad and diffuses to the capture line and binds to the α thalassemia specific antibody. Absence of an α thalassemia specific protein in a sample diffuses the α thalassemia specific antibody conjugated colloid to the control line and binds to the antibody specific to the α thalassemia specific antibody. A positive test is identified by binding of the α thalassemia specific antibody conjugated colloid at the capture line and a negative test is identified by binding of the α thalassemia specific antibody conjugated colloid at the control line.

In various exemplary embodiments according to the invention, the colloid particle is gold. In some embodiments, the colloid particle has a diameter of about 10-25 nm. In some embodiments, the α thalassemia specific protein is a γ4 protein. In various exemplary embodiments, α thalassemia specific antibody is a monoclonal antibody derived from a mouse. In yet other embodiments the α thalassemia specific antibody is a polyclonal antibody. In various exemplary embodiments, the α thalassemia specific antibody is a rabbit antibody. However it should be appreciated that the secondary antibody can be any antibody that is specific for the species from which the primary antibody is derived.

In various exemplary embodiments, the α thalassemia specific antibody is a polyclonal antibody. In various other exemplary embodiments, the α thalassemia specific antibody is a monoclonal antibody.

In various other exemplary embodiments, the invention includes a kit for identifying carriers of α thalassemia. The kit including an α thalassemia test strip and instructions for use. In various exemplary embodiments, the invention further includes a lysis buffer. In still other exemplary embodiments, the kit includes a wash buffer.

In still other exemplary embodiments according to the invention, the invention includes A method of conjugating a monoclonal antibody specific to for α thalassemia with a nanoparticle comprising obtaining an aqueous solution of a colloidal nanoparticle at a concentration of about $1\text{-}10 \times 10^{-3}$ M of HAuCl4, diluting the colloidal nanoparticle with water to bout 1:2 to about 1:50 to obtain a diluted solution, heating the diluted solution with stirring and adding sodium citrate to the heating solution to reduce the solution until a color change. In some exemplary embodiments, the sodium citrate has a concentration of about 0.1 to 1.0%.

In still other exemplary embodiments according to the invention, the invention includes a method of making a α thalassemia specific antibody coated colloid particle comprising, diluting a monocolonal antibody specific to α thalassemia with 1-10 mM sodium borate buffer pH 5-10 to obtain a solution, adding the solution to 100 ml of a 0.25 mM of colloidal nanoparticle, adjusting the pH to 7.0-10.0 by the addition of 0.01 M Na2CO3, stirring the mixture for 10-60 min and adding a 20% volume of 5% BSA in 5 mM NaCl, reacting approximately 5 minutes, centrifuging at 4° C. for approximately 10.00 to 20.00 rpm for approximately 30, resuspending a pellet in phosphate buffer, and obtaining an antibody coated colloid particle solution.

EXAMPLE 1

Purification of Hbs and Globin Chains

Hb Bart's was purified from the hemolysate of Bart's hydrops fetalis by cellulose acetate electrophoresis with an alkaline buffer solution. The Hb Bart's was separated from Hb Portland on the cellulose acetate membrane according to their net charge and size. The electrophoresis was performed at 160 V until the band of Hb Bart's was clearly separated from Hb Portland. After electrophoresis, the Hb Bart's band was cut and Hb Bart's was eluted from the membrane by soaked in 40 ml of phosphate buffer saline (PBS) pH 7.2 at 4° C. overnight. The obtained Hb Bart's was then concentrated by Vivaspin.

EXAMPLE 2

Polyclonal Antibody Production

Figure 2A:
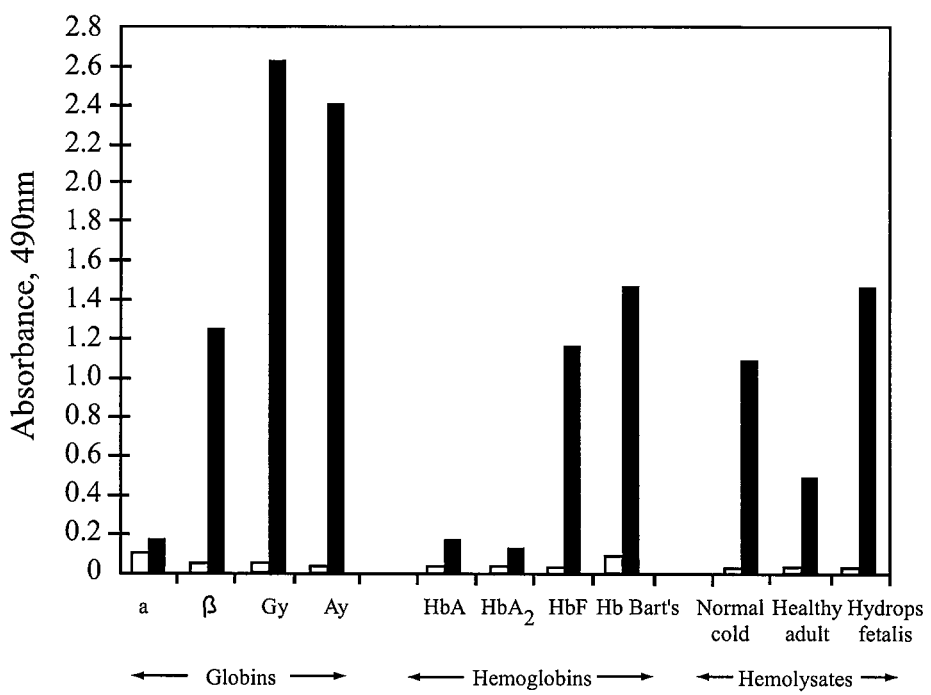
FIG. 2 A is a graph of absorbance of the reaction and extraction of lg Y from an egg with HB F (α2 γ2), Hb Barts (γ4), Hb A (α2 β2) and HB A.

Polyclonal antibodies were prepared as previously described by Jintaridth et al. (*Int J Hematol.* 2006; 83:408-414) hereby incorporated in its entirety for all purposes. After purifiAtion of the HBs and Globin chains antibodies were prepared in chicken Egg yolk. Briefly, after Hb Bart's immunization, the inventors detected anti-Hb Bart's antibodies in sera at 2 weeks after antigen immunization, and the antibodies reached their highest titer at week 4 to week 6 before declining (FIG. 1). The antibody response in the egg yolk showed the same pattern as in the serum but was delayed by 1 week. When the maximum antibody response was reached, Ig Y antibodies were extracted from the whole egg yolk. By using water dilution and sodium sulfate precipitation, we were able to extract 40 to 70 mg of IgY from an egg. The IgY extracts strongly reacted with Hb F ($\alpha_2\gamma_2$) and Hb Bart's ($\gamma_4$) and weakly reacted with Hb A ($\alpha_2\beta_2$) and Hb A ($\alpha_2\delta_2$) (FIG. 2A). The extracts also reacted with β- and γ-globin chains but did not react with α chain. The IgY anti-bodies also reacted with hemolysates from normal umbilical cord (Hbs F plus A), healthy adults (Hbs A plus $A_2$), and Hb Bart's hydrops fetalis samples (Hbs Bart's plus Portland).

Figure 2B:
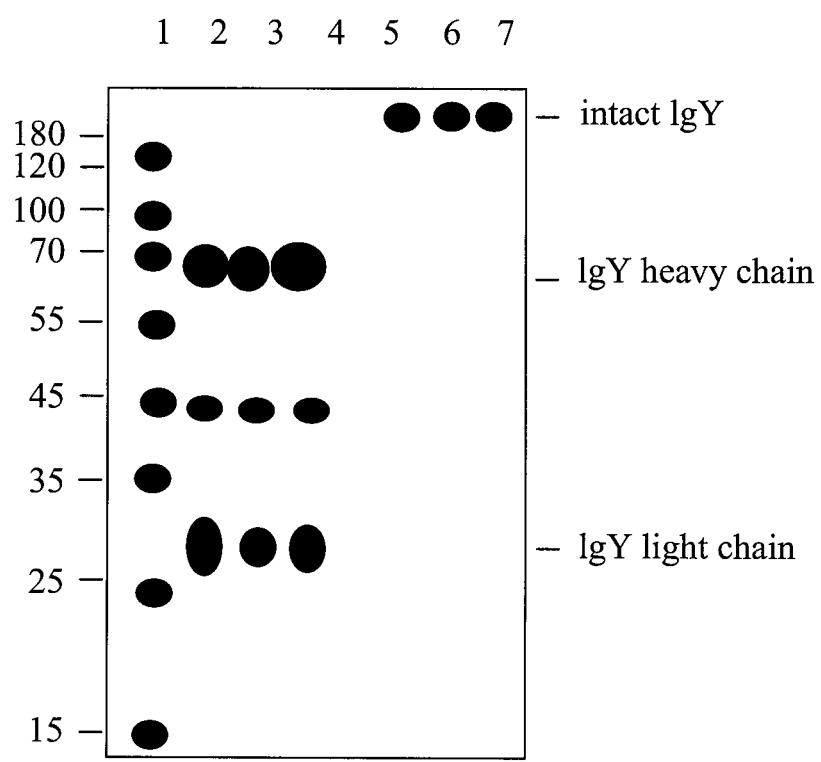
Figure 3:
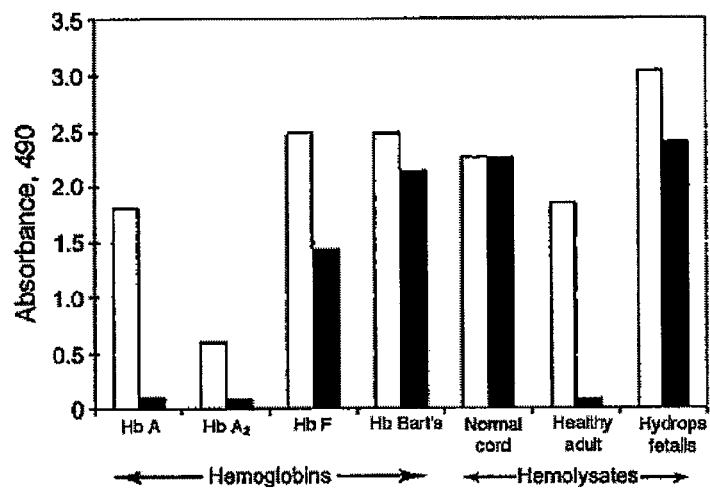
FIG. 3 is a graph of the absorbance of the various globin chains before and after affinity purification. Open bars, IgY before immunoaffinity purification; closed bars, IgY after immunoaffinity purification.

The purity of the IgY extracts was analyzed by SDS-PAGE, which under reducing conditions demonstrated IgY heavy and light chains with molecular weights of approximately 67 kd and 28 kd (FIG. 2B, lanes 2-4). Band densities quantified with a densitometer indicated that 97% of the extracted protein was IgY.

Figure 4:
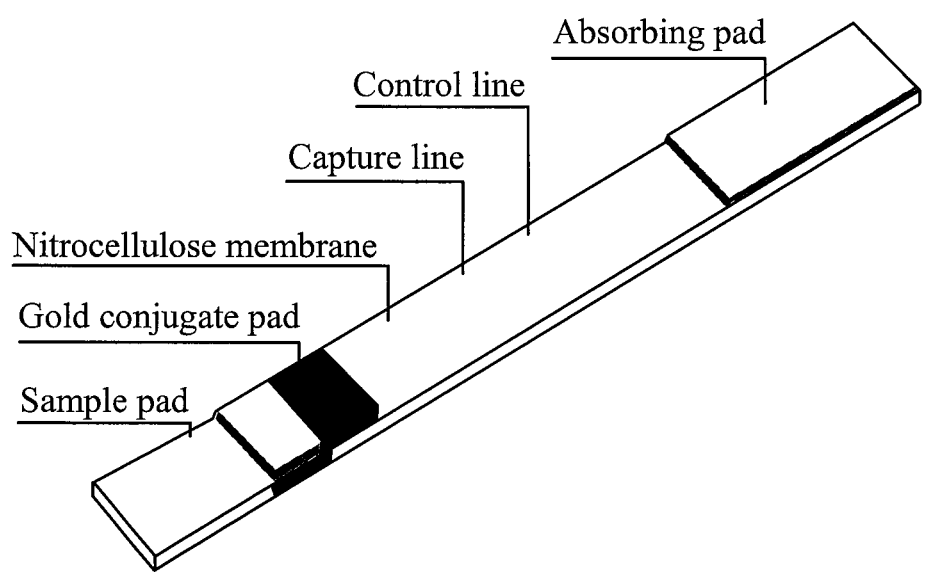
FIG. 4 is a schematic diagram showing the positioning of immunochromatographc test strip components comprising sample pad, conjugate pad, membrane, capture line, control line and absorbing pad according to one exemplary embodiment of the invention.
Figure 3:
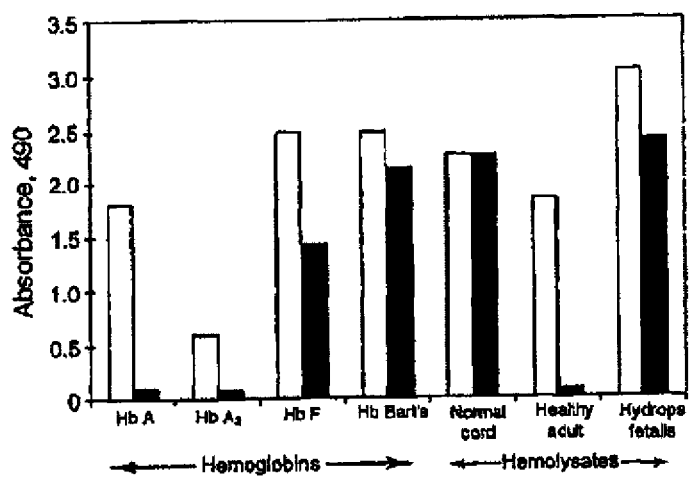
Figure 4:
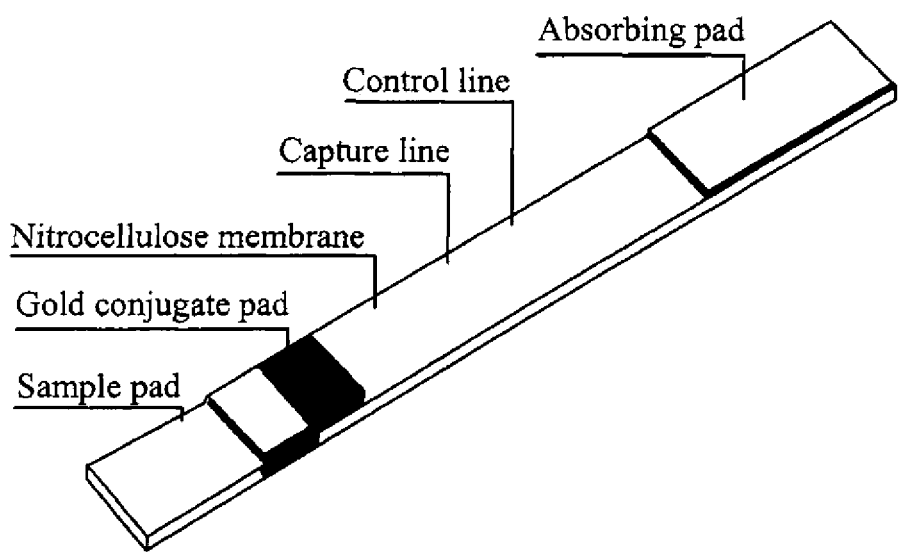
Figure 5:
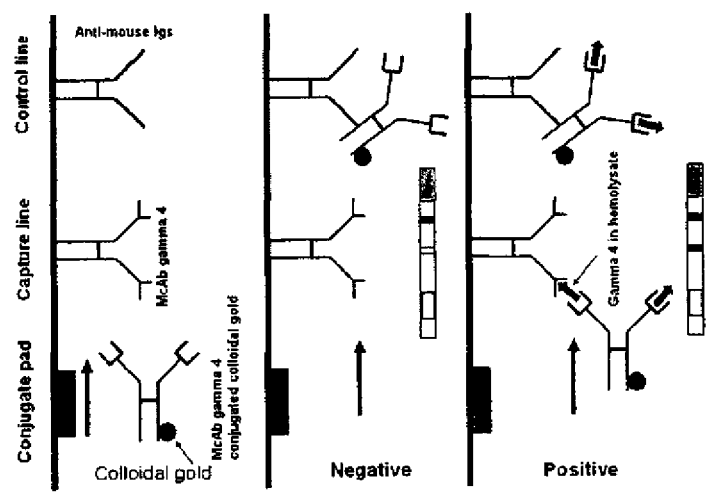

To obtain specific anti-Hb Bart's IgY, the inventors then purified the egg yolk IgY extracts by immunoadsorbent chromatography with Hb A coupled to Sepharose. The unbound fractions were collected and tested for specificity. As is shown in FIG. 4, the affinity-purified IgY reacted with Hb Bart's, Hb F, normal cord (Hbs F plus A), and Hb Bart's hydrops fetalis (Hbs Bart's plus Portland) hemolysates but not with Hb A, Hb $A_2$, or healthy adult (Hbs A plus $A_2$) hemolysate. Immunoblotting was employed to verify the specificity. The affinity-purified IgY reacted with $^G\gamma$- and $^A\gamma$-globin chains but did not react with α- and β-globin chains (data not shown).

EXAMPLE 3

Hybridoma Production

Spleen cells were collected from the mouse immunized with 1-100 μg γ4 protein and fused with P3-X63Ag8.653 myeloma cells by standard hybridoma technique using 50% polyethylene glycol. After HAT medium selection, culture supernatants were collected from the hybrid containing wells. The supernatants were then determined for antibody reactivity against γ4 protein by indirect ELISA. The hybridomas showing positive reactivity with γ4 protein but negative with other hemoglobins were selected and subcloned by limiting dilution. A hybrid clone which produced monoclonal antibody that specifically recognized the repetitive epitopes on γ4 protein was selected for developing the immunochromatographic strip test based on double antibody sandwich technique. This particular monoclonal antibody specific to γ4 protein characteristic is claimed as a unique tool for developing the assay. Further discussion and characterization of the production and screening of the mouse hybridoma and monoclonal antibody produced therefrom is provided by Makonkawkeyoon, L et al, Production of a mouse hybridoma secreting monoclonal antibody highly specific to hemoglobin Bart's (gamma4), Lab Hematol. 2006; 12(4):193-200, hereby incorporated by reference in its entirety.

EXAMPLE 4

Determination of Antibody Specificity

Specificity of affinity-purified immunoglobulin Y (IgY) antibodies. Specific antibody was obtained by purifying anti-hemoglobin (Hb) Bart's IgY on a column consisting of Hb A coupled to cyanogen bromide-activated Sepharose. The reactivity of affinity-purified unbound IgY was tested by enzyme-linked immunosorbent assay using 10 μg/mL of Hbs and hemolysates as coating antigens. FIG. 4 is a graph showing the absorbance of the reactive species before and after affinity purification.

EXAMPLE 5

Synthesis and Characterization of Colloidal Nanoparticle

Colloidal nanoparticle was synthesized using a reduced scale. An aqueous solution of colloidal such as chloroauric acid ($1\text{-}10\times10^{-3}$ M of HAuCl4, 5 ml) was diluted with 90 ml of de-ionized water or at about 1:2 to 1:50. This solution was stirred and heated until boiling and then reduced with 0.1 to 1.0% sodium citrate solution (5 ml). Heating was continued until the solution color changed to a red-purple color. The result nanoparticle has cross diameter of about 15 nm.

EXAMPLE 6

Formation Of Gold Conjugate

Monoclonal antibody specific to γ4 protein was diluted in 5 ml of 1-10 mM sodium borate buffer pH 5 to 10. This solution was then added dropwise to a stirred solution of nanoparticle 0.25 mM, 100 ml. The pH of the nanoparticle solution was pre-adjusted to 7.0-10.0 by addition of 0.01 M Na2CO3. The mixture was stirred for 10-60 min and 5 ml of 5% BSA in 5 mM NaCl solution was added. After 5 min, the solution was centrifuged at 4° C. 14,000 rpm for 30 min to remove unconjugated antibodies from the solution. The pellet was subsequently resuspended in Phosphate buffer (2% BSA in 49 mM Na2HPO4) to obtain an antibody-nanoparticle conjugate solution which had an O.D. of 40 at λ 580 nm.

EXAMPLE 7

Preparation of an Immunochromatographic Test Strip

An immunochromatographic test strip consists of four components: sample application pad, conjugate releasing pad, analytical nitrocellulose membrane, and absorbent pad (FIG. 4). The test strip was constructed as follows monoclonal antibody specific to γ4 protein (O.D. of 40-80 at λ 580 nm) was sprayed onto the conjugate releasing pad using a dispenser. The nitrocellulose membrane was laminated onto a plastic support by a laminator. Monoclonal antibody specific to γ4 protein at 0.01-2 mg/ml and rabbit anti-mouse IgG at 0.01-2 mg/ml in PBS were jetted onto a laminated nitrocellulose membrane at two separate zones, referred to as the test line and control line. Subsequently, the sprayed conjugate pad and jetted membrane were incubated for 4 h at 37° C. and then dried in a desiccator at room temperature. After drying, the components of the strip test (the sample application pad, the sprayed conjugate releasing pad, the jetted nitrocellulose membrane, and the absorbent pad) were assembled and then cut into individual strips (4.0 mm/strip).

EXAMPLE 8

Preparation of an Immunochromatographic Test Strip

An immunochromatographic strip test contains at least following components but not limit to:
1) Solution for break off red blood cell can be choice(s) of TWEEN 20 Polysorbate 20, SDS, NP-40 nonyl phenoxypolyethoxylethanol or TRITON X100 octyl phenol ethoxylate, at the amount of 1 to 10, which able to react in whole blood solution and not necessary to separate out red blood cell prior to this step;

2) Buffer for washing strip is phosphate buffered saline and 0.01 to 5% TWEEN 20 Polysorbate 20;

3) Immunochromatographic strip for detection of γ4 proteins as described above which its capture line comprises a small strip of membrane holding monoclonal antibody specific to γ4 proteins coated on nanoparticle; and its control line comprises of small strip of membrane holding 0.1 to 10 mg/ml antibody specific to mouse immunoglobulin;

4) Working plate with flat bottom; and (5) Wash bottle.

EXAMPLE 9

Screening Process For α-Thalassemia Carrier Using Immunochromatographic Strip

Allow strip test and whole blood specimen to equilibrate to room temperature (15-30° C.) prior to testing:

1) Add approximately 100 μl of EDTA blood into 96-well plate;
2) Add approximately 100 μl of Lysis buffer into the sample and mix thoroughly for 3 to 4 times using autopipette;
3) Bring the pouch to room temperature before opening it. Remove the test strip from the sealed pouch and use it as soon as possible;
4) With arrows pointing toward the sample well, immerse the test strip vertically in the hemolyzed blood for 2 minutes. Do not pass the maximum line (MAX) on the strip test when immersing the strip;
5) Remove the strip from blood sample and clean it with washing buffer by using wash bottle;
6) It is important that the background is clear before the result is read.

EXAMPLE 10

Interpretation Of Result(s)

Figure 5:
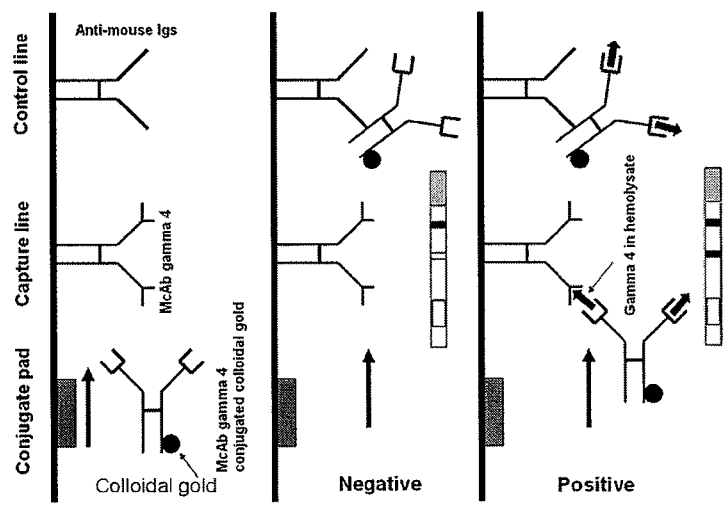
FIG. 5 is a diagram illustrating conjugate actions of an immunochromatographic strip test for control, negative and positive reading according to the exemplary embodiment of the invention shown in FIG. 4.

As illustrated in FIG. 5, a positive reading will show 2 purple bands; one at control line and another one at capture line and negative reading shows only single purple band at the control line. FIG. 5 illustrates the molecular basis of the unused, negative and positive test strip readings. The left column shows the unchallenged test strip with the conjugated α-thallasemia specific antibody at the storage position on the conjugate pad. The middle column shows a negative reading where the unbound conjugated antibody binds to the rabbit anti-mouse secondary antibody immobilized on the nitrocellulose membrane at the control line. the third column shows the conjugated antibody bound to a γ4 antigen and also bound to the unconjugated anti-γ4 antibody immobilized on the nitrocellulose membrane of the test strip at the capture or positive reading zone.

While this invention has been described in conjunction with the various exemplary embodiments outlined above, various alternatives, modifications, variations, improvements, and/or substantial equivalents, whether known or that are or may be presently unforeseen, may become apparent to those having at least ordinary skill in the art. Thus, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents of these exemplary embodiments

REFERENCES

1. Huisman T H J, Jonxis J H P. The Hemoglobinopathies: Techniques of Identification. New York, N.Y.: Marcel Dekker; 1977.
2. Abraham E C, Reese A, Stallings M, Huisman T H. Separation of human hemoglobins by DEAE-cellulose chromatography using glycine-KCN—NaCl developers. Hemoglobin. 1976-1977; 1:27-44.
3. Kutlar F, Gu L H, Hu H, Huisman T H. Quantitation of Hb Bart's, H, Portland-I, Portland-II and constant spring by anion-exchange high-performance liquid chromatography. J Chromatogr. 1989; 487:265-274.

What is claimed is:

1. A method of using the immunochromatographic strip for screening an α-thalassemia carrier, comprising:
   (1) lysing red blood cells of a blood sample obtained from a subject;
   (2) applying an aliquot of the lysed red blood cells obtained in (1) to said strip;
   (3) substantially removing the applied aliquot by washing the strip; and
   (4) determining whether the subject is an α-thalassemia carrier based on a positive chromatographic result or a negative chromatographic result that is obtained from (1)-(3);
   wherein the positive chromatographic result indicates that the subject is an α-thalassemia carrier;
   wherein the positive chromatographic result is chromatographically distinguishable on the immunochromatographic strip from the negative chromatographic result; and
   wherein the immunochromatographic strip comprises:
      a sample application pad;
      a conjugate releasing pad;
      a nitrocellulose membrane; and
      an absorbent pad;
      wherein said sample application pad, said conjugate releasing pad, said nitrocellulose membrane, and said absorbent pad are in connected association with one another so as to form the immunochromatographic strip;
      wherein the conjugate releasing pad comprises a colloid particle that is conjugated to an antibody specific for an α-thalassemia protein;
      wherein the nitrocellulose membrane comprises an unconjugated antibody specific for the α-thalassemia protein that is immobilized at a capture line and an antibody specific to the α-thalassemia protein specific antibody that is immobilized at a control line, the control line being located distal to the capture line; and
      wherein the positive chromatographic result is obtained by binding of an α-thalassemia protein to the antibody conjugated to the colloid particle to form a complex and further binding of the complex to the unconjugated antibody so as to produce a first visually identifiable signal at the capture line, and the negative chromatographic result is obtained by unbound antibody conjugated to the colloid particle to the antibody specific to the α-thalassemia protein specific antibody so as to produce a second visually identifiable signal at the control line.

2. An immunochromatographic strip for screening an α-thalassemia carrier comprises:
- a sample application pad;
- a conjugate releasing pad;
- a nitrocellulose membrane; and
- an absorbent pad;

wherein said sample application pad, said conjugate releasing pad, said nitrocellulose membrane, and said absorbent pad are in connected association with one another so as to form the immunochromatographic strip;

wherein the conjugate releasing pad comprises a colloid particle that is conjugated to an antibody specific for an α-thalassemia protein;

wherein the nitrocellulose membrane comprises an unconjugated antibody specific for the α-thalassemia protein that is immobilized at a capture line and an antibody specific to the α-thalassemia protein specific antibody that is immobilized at a control line, the control line being located distal to the capture line; and wherein a positive chromatographic result is obtained by binding of an α-thalassemia protein to the antibody conjugated to the colloid particle to form a complex and further binding of the complex to the unconjugated antibody so as to produce a first visually identifiable signal at the capture line, and a negative chromatographic result is obtained by binding of unbound antibody conjugated to the colloid particle to the antibody specific to the α-thalassemia protein specific antibody so as to produce a second visually identifiable signal at the control line.

3. The immunochromatographic strip of claim 2, wherein the α-thalassemia specific protein is a γ4 protein.

4. The immunochromatographic strip of claim 2, wherein the sample application pad partially overlaps the conjugate releasing pad and is separated from abutting contact with the nitrocellulose membrane thereby, wherein the conjugate releasing pad partially overlaps the nitrocellulose membrane and is separated from abutting contact with the absorbent pad thereby, and wherein the absorbent pad partially overlaps the nitrocellulose membrane.

* * * * *

UNITED STATES PATENT AND TRADEMARK OFFICE
CERTIFICATE OF CORRECTION

PATENT NO. : 8,563,330 B2
APPLICATION NO. : 12/053449
DATED : October 22, 2013
INVENTOR(S) : Watchara Kasinrerk et al.

It is certified that error appears in the above-identified patent and that said Letters Patent is hereby corrected as shown below:

DRAWINGS

| Sheet | Fig. | PTO | Should Read |
|---|---|---|---|
| 3 and 4 | 4 and 5 | Fig. 5 is on sheet 3 and Fig. 4 is on sheet 4 | -- Fig. 4 should be on sheet 3. Fig. 5 should be on sheet 4. -- (See Attached Sheets) |

SPECIFICATION

| Column | Line | PTO | Should Read |
|---|---|---|---|
| 2 | 60 | "a thalassemia specific" | -- α thalassemia specific -- |
| 2 | 64 | "binding of the cc thalassemia" | -- binding of the α thalassemia -- |
| 3 | 5 | "a, thalassemia" | -- α, thalassemia -- |
| 3 | 19 | "for a thalassemia" | -- for α thalassemia -- |
| 3 | 33 | "solution lo 100 ml" | -- solution to 100 ml -- |
| 3 | 35 | "Na2C03" | -- Na2CO3 -- |
| 6 | 32 | "10.00 to 20.00 rpm" | -- 10,00 to 20,00 rpm -- |

Signed and Sealed this
Eighteenth Day of February, 2014

Michelle K. Lee
*Deputy Director of the United States Patent and Trademark Office*